(12) United States Patent
Tokida

(10) Patent No.: US 11,596,310 B2
(45) Date of Patent: Mar. 7, 2023

(54) IMAGE DIAGNOSIS CATHETER

(71) Applicant: TERUMO KABUSHIKI KAISHA, Tokyo (JP)

(72) Inventor: Masanori Tokida, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 183 days.

(21) Appl. No.: 16/728,563

(22) Filed: Dec. 27, 2019

(65) Prior Publication Data

US 2020/0129072 A1 Apr. 30, 2020

Related U.S. Application Data

(63) Continuation of application No. PCT/JP2018/024580, filed on Jun. 28, 2018.

(30) Foreign Application Priority Data

Jun. 29, 2017 (JP) .............................. JP2017-127631

(51) Int. Cl.
*A61B 5/00* (2006.01)
*A61B 8/08* (2006.01)
(Continued)

(52) U.S. Cl.
CPC .......... *A61B 5/0084* (2013.01); *A61B 5/0066* (2013.01); *A61B 5/6852* (2013.01);
(Continued)

(58) Field of Classification Search
CPC ... A61B 5/0084; A61B 5/6852; A61B 5/0066; A61B 8/12; A61B 8/44
See application file for complete search history.

(56) References Cited

U.S. PATENT DOCUMENTS

2013/0006104 A1  1/2013 Misuhashi et al.
2015/0005626 A1  1/2015 Kaneko
(Continued)

FOREIGN PATENT DOCUMENTS

CN  102834044 A    12/2012
EP    0092080 A1 * 10/1983  ............... A61B 8/12
(Continued)

OTHER PUBLICATIONS

An English Translation of the International Search Report (Form PCT/ISA/210) and the Written Opinion of the International Searching Authority (Form PCT/ISA/237) dated Jul. 31, 2018, by the Japanese Patent Office in corresponding International Application No. PCT/JP2018/024580. (11 pages).
(Continued)

*Primary Examiner* — Joseph M Santos Rodriguez

(74) *Attorney, Agent, or Firm* — Buchanan Ingersoll & Rooney PC

(57) ABSTRACT

An image diagnosis catheter includes a rotatable drive shaft, a sheath into which the drive shaft is inserted, a housing provided at a distal end of the drive shaft and accommodating an ultrasound transmitter and receiver and an optical transmitter and receiver, and a positioning member fixed to the housing and fixing a relative position of the optical transmitter and receiver with respect to the ultrasound transmitter and receiver.

20 Claims, 12 Drawing Sheets

(51) Int. Cl.
*A61B 8/12* (2006.01)
*A61B 8/00* (2006.01)

(52) U.S. Cl.
CPC .............. *A61B 8/0841* (2013.01); *A61B 8/12* (2013.01); *A61B 8/445* (2013.01); *A61B 8/54* (2013.01)

(56) References Cited

U.S. PATENT DOCUMENTS

| | | | |
|---|---|---|---|
| 2015/0005628 A1 | 1/2015 | Itoh et al. | |
| 2017/0079617 A1* | 3/2017 | Yamamoto | ........... A61B 8/4494 |
| 2020/0037989 A1* | 2/2020 | Taniguchi | ........... A61B 8/4494 |

FOREIGN PATENT DOCUMENTS

| | | | | |
|---|---|---|---|---|
| EP | 2 832 301 A1 | 2/2015 | | |
| EP | 2 832 302 A1 | 2/2015 | | |
| JP | 2015164660 A | 9/2015 | | |
| WO | 2013145637 A1 | 10/2013 | | |
| WO | 2013145689 A1 | 10/2013 | | |
| WO | WO-2016047772 A1 * | 3/2016 | ......... A61B 5/02007 |

OTHER PUBLICATIONS

International Search Report (PCT/ISA/210) and translation and Written Opinion (PCT/ISA/237) dated Jul. 31, 2018, by the Japanese Patent Office as the International Searching Authority for International Application No. PCT/JP2018/024580.

Office Action (The First Office Action) dated Jul. 29, 2022, by the State Intellectual Property Office of People's Republic of China in corresponding Chinese Patent Application No. 201880043810.1 and an English Translation of the Office Action. (17 pages).

* cited by examiner

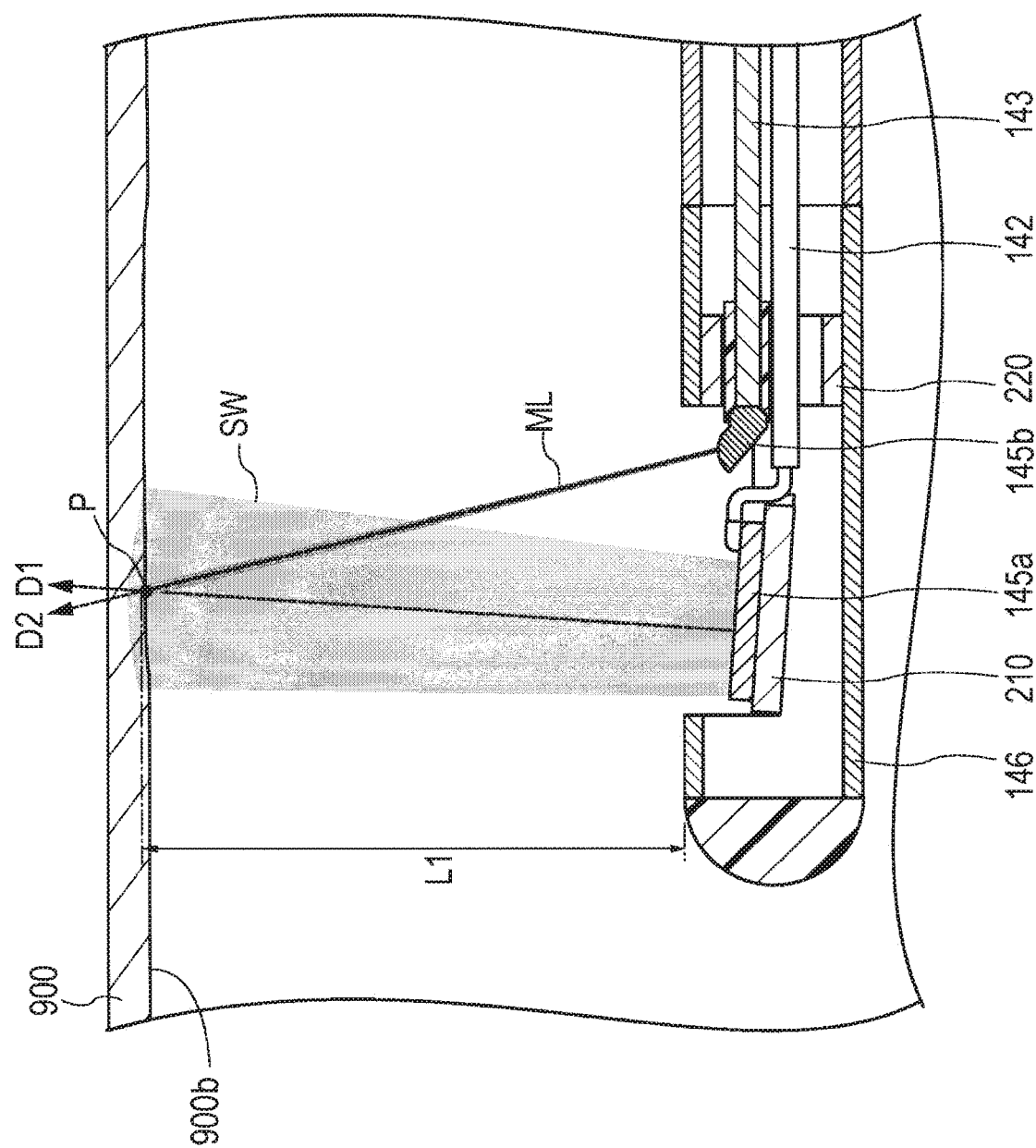

IMAGE DIAGNOSIS CATHETER

CROSS-REFERENCES TO RELATED APPLICATIONS

This application is a continuation of International Application No. PCT/JP2018/024580 filed on Jun. 28, 2018, and claims priority to Japanese Application No. 2017-127631 filed on Jun. 29, 2017, the entire content of both of which is incorporated herein by reference.

FIELD OF THE INVENTION

The present invention generally relates to an image diagnosis catheter.

BACKGROUND DISCUSSION

In recent years, as a medical apparatus used to acquire a diagnostic image for diagnosing a diseased site in a living body, a dual-type image diagnosis catheter having functions of both an intra vascular ultra sound (IVUS) diagnosis method and an optical coherence tomography (OCT) diagnosis method has been developed. An example is disclosed in Japanese Patent Application Publication No. 2015-164660.

The dual-type image diagnosis catheter has a drive shaft provided with an ultrasound transmitter and receiver and an optical transmitter and receiver at a distal end, and a sheath provided with a lumen into which a drive shaft is rotatably inserted. When obtaining a tomographic image with the image diagnosis catheter, the sheath is inserted into a biological lumen, and moved rearward while rotating the drive shaft within the sheath. Therefore, an operation for moving the drive shaft from a distal end side to a proximal end side, so-called a pull-back operation, or a push-in operation for pushing the drive shaft toward the distal end side is performed. Simultaneously with this operation, the ultrasound transmitter and receiver transmits an ultrasound toward a wall of the biological lumen and receives a reflected wave reflected on the wall of the biological lumen. In addition, the optical transmitter and receiver simultaneously transmits light toward the wall of the biological lumen and receives a reflected light reflected on the wall of the biological lumen.

SUMMARY

The dual-type image diagnosis catheter disclosed in Japanese Patent Application Publication No. 2015-164660 is not provided with a mechanism for fixing a relative position of the optical transmitter and receiver with respect to the ultrasound transmitter and receiver. Therefore, it is difficult to maintain a transmission direction of light transmitted from the optical transmitter and receiver in a fixed direction with respect to a transmission direction of the ultrasound transmitted from the ultrasound transmitter and receiver. Therefore, it is difficult to maintain the relative position of light with respect to the ultrasound of each image diagnosis catheter within a desired tolerance at the time of manufacture (assemble), for example.

An image diagnosis catheter is disclosed that is capable of maintaining a transmission direction of light in a fixed direction with respect to a transmission direction of the ultrasound.

The disclosed image diagnosis catheter includes a rotatable drive shaft, a sheath into which the drive shaft is inserted, a housing provided at a distal end of the drive shaft and accommodating an ultrasound transmitter and receiver and an optical transmitter and receiver, and a positioning member fixed to the housing and fixing a relative position of the optical transmitter and receiver with respect to the ultrasound transmitter and receiver.

The disclosed image diagnosis catheter is configured so that a relative position of the optical transmitter and receiver with respect to the ultrasound transmitter and receiver is fixed. Therefore, a transmission direction of light can be kept in a fixed direction with respect to a transmission direction of the ultrasound.

According to another aspect, an image diagnosis catheter that is positionable in a living body to acquire a diagnostic image for diagnosing a site in the living body comprises a rotatable elongated tubular body that rotates about a rotational axis, an electrical signal cable positioned inside the tubular body; an optical fiber positioned inside the tubular body; an elongated sheath in which is positioned the elongated tubular body; and a housing mounted at the distal end of the tubular body, wherein the housing includes an opening at the distal end portion of the housing. A ultrasound transmitter and receiver is connected to the electrical signal cable and is configured to transmit and receive ultrasound through the opening in the housing, and an optical transmitter and receiver is connected to the optical fiber and configured to transmit and receive light through the opening in the housing. A positioning member is fixed inside the housing at a location proximal of the opening in the housing, and the positioning member houses both the ultrasound transmitter and receiver and the optical transmitter and receiver so that the ultrasound transmitter and receiver and the optical transmitter and receiver are positionally fixed relative to one another.

BRIEF DESCRIPTION OF THE DRAWINGS

FIG. 2(A) is a side view of the image diagnosis catheter before performing a pull-back operation (thinning operation), and FIG. 2(B) is a side view of the image diagnosis catheter when the pull-back operation is performed.

FIG. 10 is a schematic diagram illustrating a state where a signal transmitter and receiver transmits an ultrasound and light in a biological lumen.

DETAILED DESCRIPTION

Set forth below with reference to the accompanying drawings is a detailed description of embodiments of a stent and a stent manufacturing method representing examples of the inventive image diagnosis catheter disclosed here. The dimensions or scales on the drawings may be exaggerated or different from actuality/reality for convenience of description and illustration. The following description does not limit the technical scope and terms used in the aspects.

Figure 1:
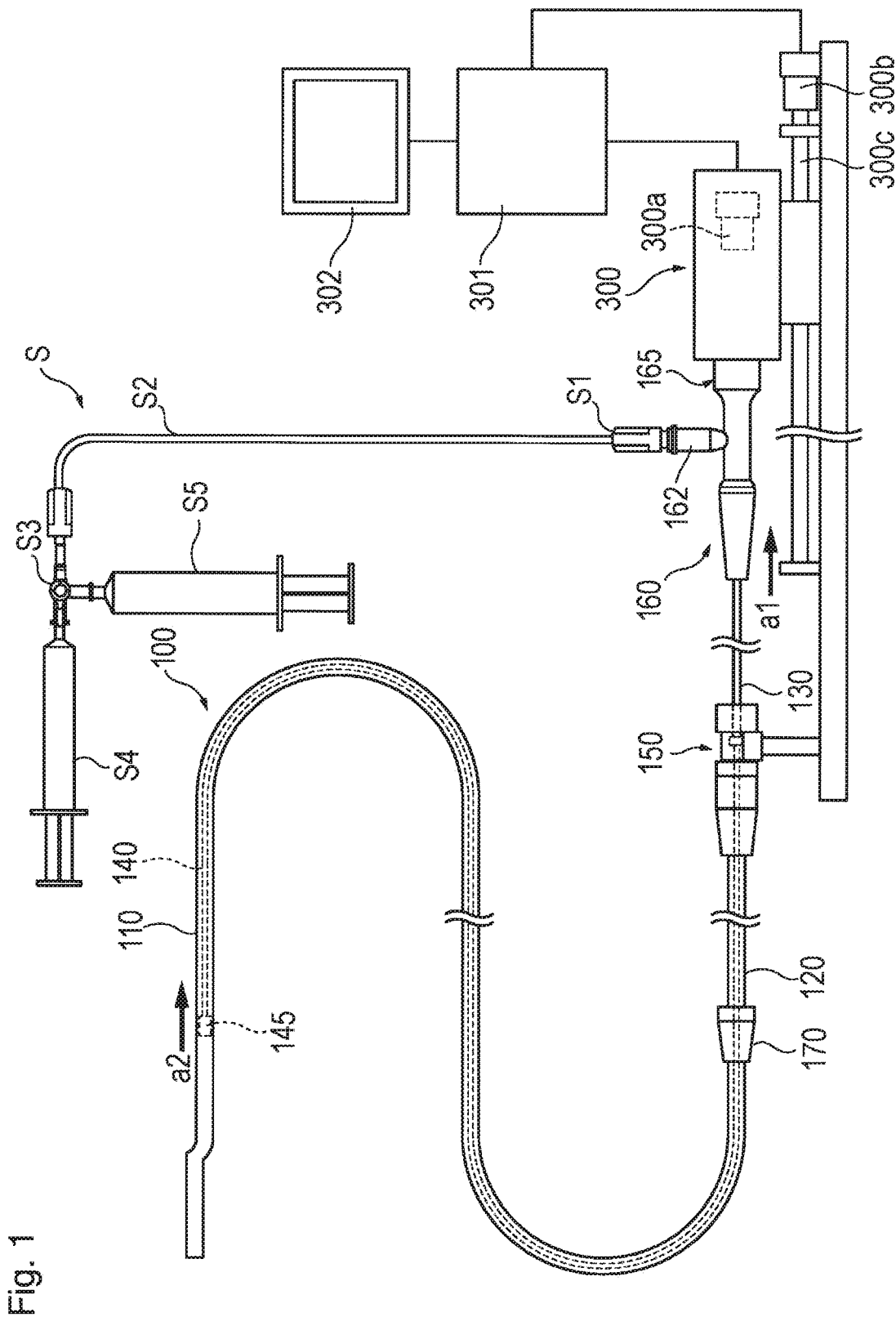
FIG. 1 is a plan view illustrating a state where an external device is connected to an image diagnosis catheter according to an embodiment of the present invention.
Figure 3:
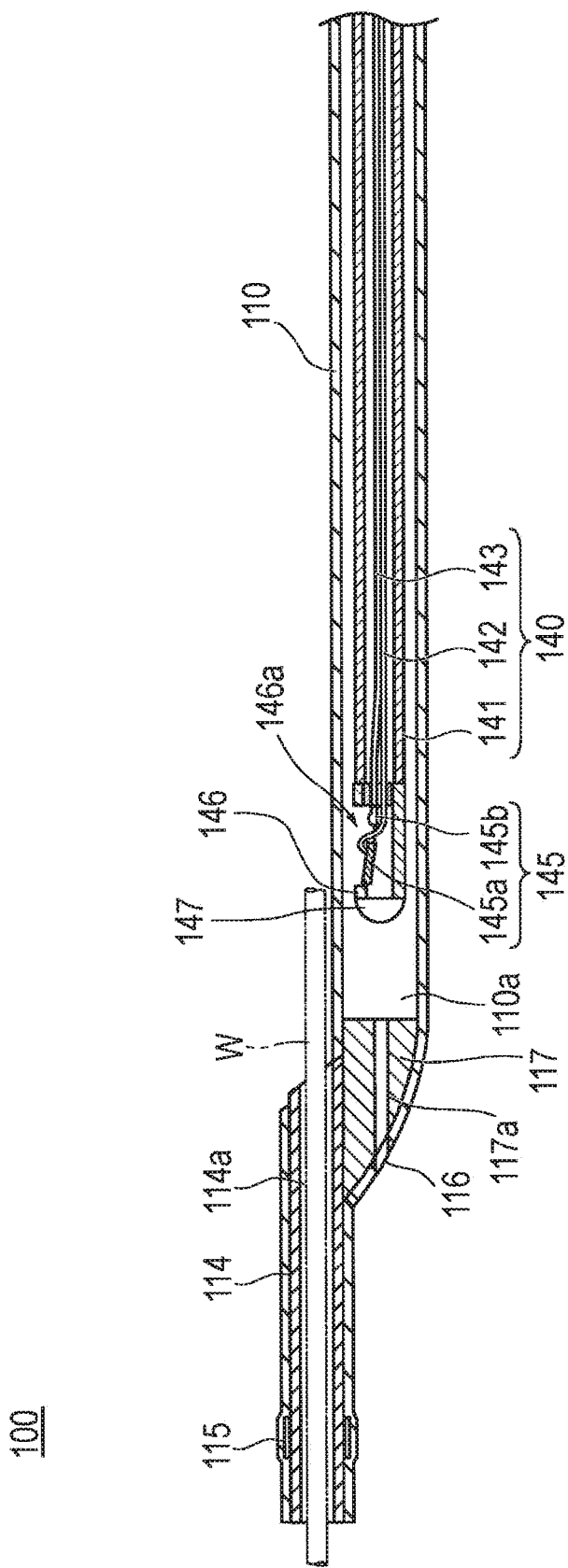
FIG. 3 is an enlarged cross-sectional view illustrating a configuration of a distal end of the image diagnosis catheter according to the embodiment.
Figure 4:
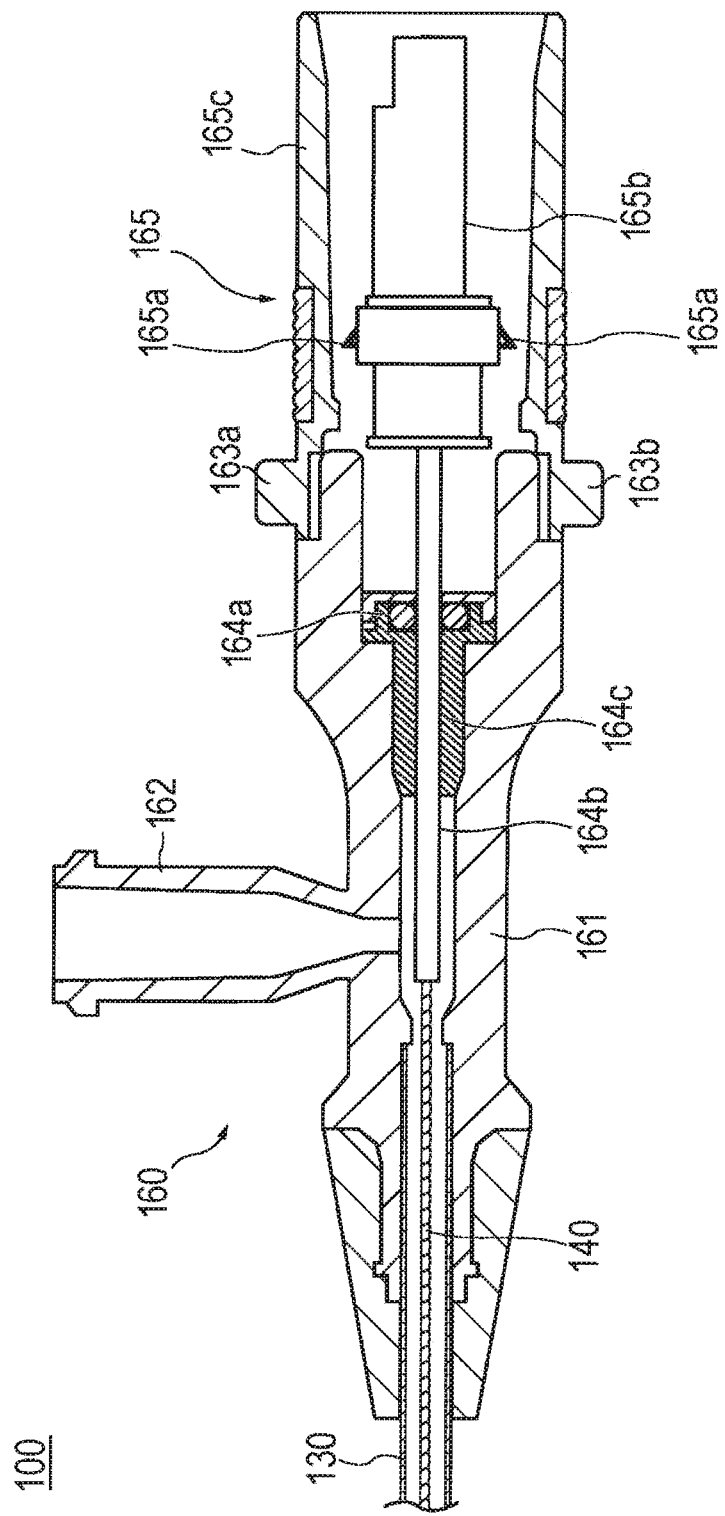
FIG. 4 is an enlarged cross-sectional view illustrating a configuration of a proximal end of the image diagnosis catheter according to the embodiment.
Figure 11:
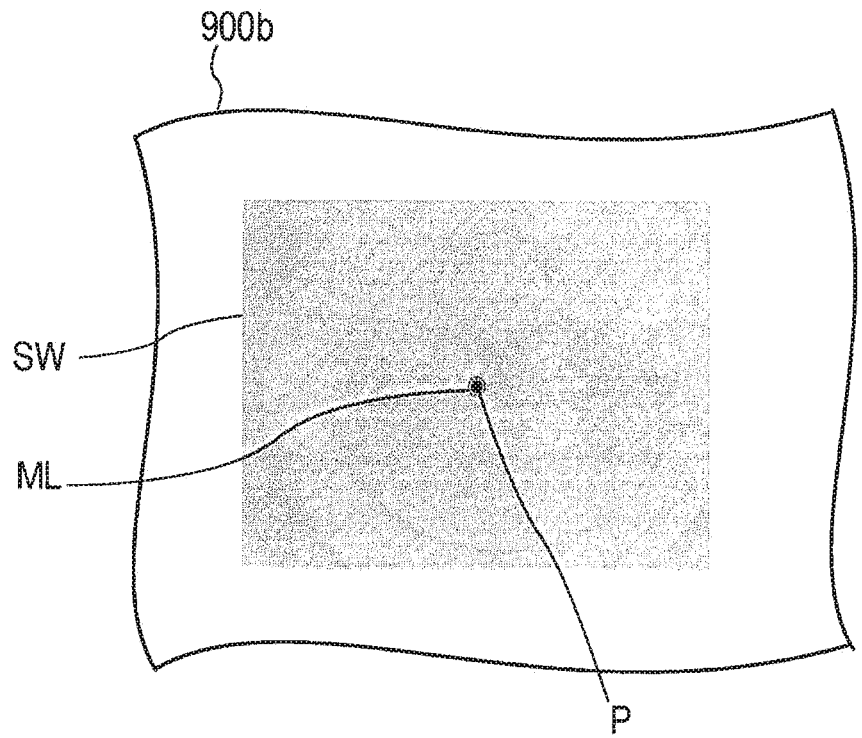
FIG. 11 is a diagram schematically illustrating a region on which an ultrasound strikes and a region on which light strikes on a wall of the biological lumen.

FIG. 1 is a plan view illustrating a state where an external device 300 is connected to an image diagnosis catheter 100 according to the present embodiment representing one example of the disclosed image diagnosis catheter. FIG. 2 is a diagram schematically illustrating an overall configuration of the image diagnosis catheter 100. FIG. 3 is a diagram illustrating a configuration of a distal end of the image diagnosis catheter 100. FIG. 4 is a diagram illustrating a configuration of a proximal end of the image diagnosis catheter 100. In addition, FIGS. 5 to 8 are diagrams for describing a positioning mechanism of an ultrasound transmitter and receiver 145a and an optical transmitter and receiver 145b, which are main parts of the image diagnosis catheter 100. In addition, FIGS. 9 to 11 are diagrams for describing an example of use of the image diagnosis catheter 100.

The image diagnosis catheter 100 according to the present embodiment is a dual-type image diagnosis catheter having both functions of an intra vascular ultra sound (IVUS) diagnosis method and an optical coherence tomography (OCT) diagnosis method. In the dual-type image diagnosis catheter 100, there are three types of modes: a mode for acquiring a tomographic image only by IVUS, a mode for acquiring a tomographic image only by OCT, and a mode for acquiring a tomographic image by IVUS and OCT. These modes can be switched and used. As illustrated in FIG. 1, the image diagnosis catheter 100 is driven by being connected to the external device 300.

The image diagnosis catheter 100 will be described with reference to FIGS. 1 to 4.

Figure 2A:
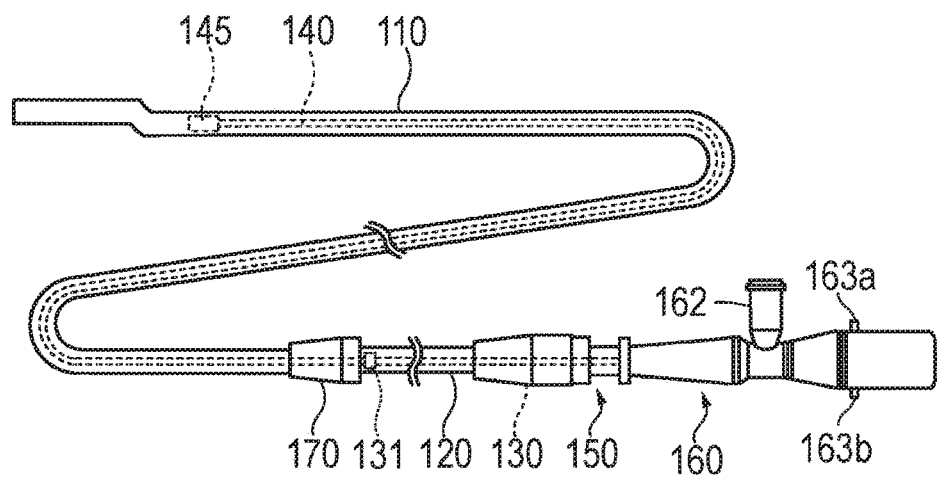
FIGS. 2(A) and 2(B) are diagrams schematically illustrating an overall configuration of the image diagnosis catheter according to the embodiment.
Figure 2B:
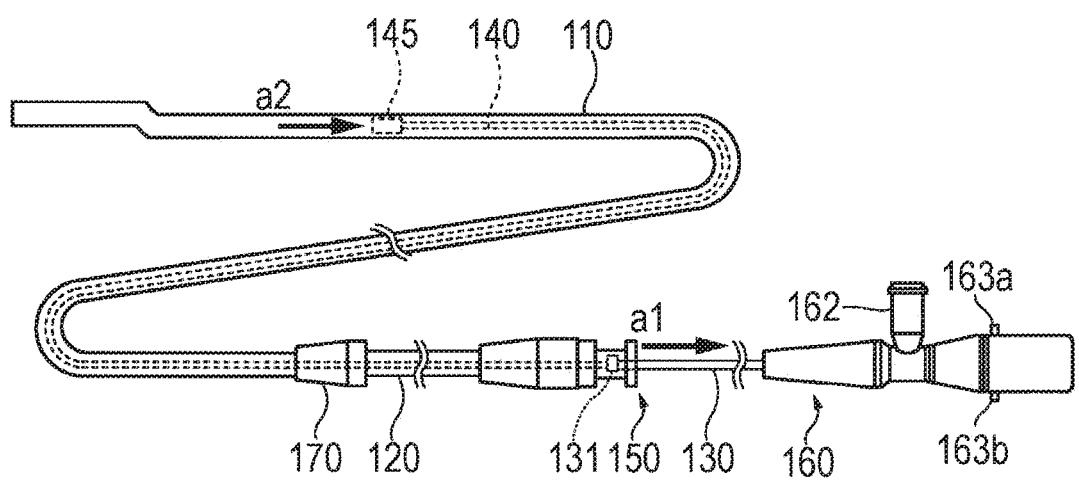

As illustrated in FIGS. 1, 2(A), and 2(B), briefly, the image diagnosis catheter 100 includes a sheath 110 to be inserted into a body-cavity of a living body, an outer tube 120 provided on a proximal end of the sheath 110, an inner shaft 130 inserted into the outer tube 120 so as to be movable forward and backward, a drive shaft 140 rotatably provided in the sheath 110 having a signal transmitter and receiver 145 transmitting and receiving signals at a distal end, a unit connector 150 provided on the proximal end of the outer tube 120 and configured to receive the inner shaft 130, and a hub 160 provided on the proximal end of the inner shaft 130.

In the following description, a side inserted into the body-cavity of the image diagnosis catheter 100 is referred to as a distal end or a distal end side. A hub 160 side provided in the image diagnosis catheter 100 is referred to as a proximal end or a proximal end side. An extending direction of the sheath 110 is referred to as an axial direction.

As illustrated in FIG. 2(A), the drive shaft 140 extends to the inside of the hub 160 through the sheath 110, the outer tube 120 connected to the proximal end of the sheath 110, and the inner shaft 130 inserted into or positioned inside the outer tube 120.

The hub 160, the inner shaft 130, the drive shaft 140, and the signal transmitter and receiver 145 are connected to each other so as to move forward and backward integrally (together) in the axial direction. Therefore, for example, when the hub 160 is pushed toward the distal end side, the inner shaft 130 connected to the hub 160 is pushed into the outer tube 120 and the unit connector 150, and the drive shaft 140 and the signal transmitter and receiver 145 move inside the sheath 110 toward the distal end side. For example, when the operation of pulling the hub 160 toward the proximal end side is performed, the inner shaft 130 is pulled out from the outer tube 120 and the unit connector 150 as illustrated by an arrow a1 in FIGS. 1 and 2(B). The drive shaft 140 and the signal transmitter and receiver 145 move inside the sheath 110 toward the proximal end side as indicated by an arrow a2.

As illustrated in FIG. 2(A), when the inner shaft 130 is pushed most into the distal end side, a distal portion of the inner shaft 130 reaches the vicinity of a relay connector 170. At this time, the signal transmitter and receiver 145 is located in the vicinity of the distal end of the sheath 110. The relay connector 170 is a connector that connects the sheath 110 and the outer tube 120.

As illustrated in FIG. 2(B), a connector 131 for preventing disconnection is provided at the distal end of the inner shaft 130. The connector 131 for preventing disconnection has a function of preventing the inner shaft 130 from coming out of the outer tube 120. When the hub 160 is most pulled out toward the proximal end side, that is, when the inner shaft 130 is most pulled out from the outer tube 120 and the unit connector 150, the connector 131 for preventing disconnection is configured to be caught at a predetermined position on an inner wall of the unit connector 150.

As illustrated in FIG. 3, the drive shaft 140 is provided with a flexible tubular body 141, and an electric signal cable 142 (corresponding to "signal line") and an optical fiber 143 connected to the signal transmitter and receiver 145 are disposed therein. The tubular body 141 can be configured to include, for example, a multilayer coil having different winding directions around the axis. Examples of the material constituting the coil include stainless steel and Ni—Ti (nickel and titanium) alloy. In the present embodiment, the electric signal cable 142 is provided with two signal lines 142a and 142b that are electrically connected to electrode terminals 165a provided in a connector portion 165 described later.

The signal transmitter and receiver 145 includes the ultrasound transmitter and receiver 145a that transmits and receives the ultrasound and the optical transmitter and receiver 145b that transmits and receives light.

The ultrasound transmitter and receiver 145a is provided with a transducer, and has a function of transmitting the ultrasound based on a pulse signal into the body-cavity and receiving the ultrasound reflected from a biological tissue in the body-cavity. The ultrasound transmitter and receiver 145a is electrically connected to the electrode terminal 165a (refer to FIG. 4) via the electric signal cable 142.

As the transducer provided in the ultrasound transmitter and receiver 145a, for example, a piezoelectric material such as ceramics or quartz can be used.

The optical transmitter and receiver 145b continuously transmits a transmitted measurement light ML into the body-cavity and continuously receives a reflected light from the biological tissue in the body-cavity. The optical transmitter and receiver 145b is provided at the distal end of the optical fiber 143, and has an optical element having a lens function for condensing light and a reflection function for reflecting light. In the present embodiment, the optical element is formed of a ball lens.

The signal transmitter and receiver 145 is accommodated in a housing 146. The proximal end of the housing 146 is connected to the drive shaft 140. The housing 146 has a shape in which an opening portion (opening) 146a is provided on a cylindrical surface of a cylindrical metal pipe so as not to hinder the progress of the ultrasound transmitted and received by the ultrasound transmitter and receiver 145a and light transmitted and received by the optical transmitter and receiver 145b. The housing 146 can be formed by, for example, laser processing. The housing 146 may be formed by cutting from a metal mass, metallic powder injection molding (MIM), or the like.

A distal member 147 is provided at the distal end of the housing 146. The distal member 147 has a substantially hemispherical outer shape. The distal member 147 is formed in a hemispherical shape, so that friction and catching with the inner surface of the sheath 110 can be suppressed. The distal member 147 may be formed of a coil, for example. In addition, the distal member 147 may not be provided at the distal end of the housing 146.

The sheath 110 is provided with a lumen 110a into which the drive shaft 140 is inserted or positioned so as to be movable forward and backward. A guide wire insertion member 114 provided with a guide wire lumen 114a that is parallel to the lumen 110a provided in the sheath 110 and into which a second guide wire W to be described later can be inserted is attached to the distal portion of the sheath 110. The sheath 110 and the guide wire insertion member 114 can be integrally formed by heat-welding or the like. The guide wire insertion member 114 is provided with a marker 115 having X-ray contrast properties. The marker 115 is formed of a metal pipe having high radiopacity such as Pt and Au. Note that, for the purpose of improving the mechanical strength, an alloy in which Ir is mixed with Pt aforementioned may be used. Furthermore, the marker 115 may be formed of a metal coil instead of a metal pipe.

A communication hole 116 that communicates the inside and the outside of the lumen 110a is formed at the distal portion of the sheath 110. In addition, a reinforcing member 117 for firmly joining and supporting the guide wire insertion member 114 is provided at the distal portion of the sheath 110. The reinforcing member 117 is formed with a communication passage 117a that communicates the inside of the lumen 110a disposed on the proximal end from the reinforcing member 117 and the communication hole 116. The reinforcing member 117 may not be provided at the distal portion of the sheath 110.

The communication hole 116 is a priming solution discharge hole for discharging a priming solution. When the image diagnosis catheter 100 is used, priming processing of filling the sheath 110 with the priming solution is performed. For example, in a case where ultrasound SW is transmitted without filling the sheath 110 with the priming solution, due to a large difference in acoustic impedance between a matching layer disposed on the surface of the transducer of the ultrasound transmitter and receiver 145a and the air, the ultrasound SW is reflected at the interface between the matching layer and the air, and there is a possibility that the ultrasound SW cannot reach a wall of a biological lumen 900 deeply. On the other hand, by filling the sheath 110 with the priming solution, since the priming solution has an acoustic impedance value close to that of the matching layer, the ultrasound SW can reach the wall of the biological lumen 900 deeply. When performing the priming processing, the priming solution can be discharged to the outside by way of the communication hole 116 and the gas such as air can be discharged from the inside of the sheath 110 together with the priming solution.

The distal portion of the sheath 110, which is the range in which the signal transmitter and receiver 145 moves in the axial direction of the sheath 110, includes a window portion that is formed to have higher permeability of inspection waves such as light and an ultrasound than other portions.

The sheath 110, the guide wire insertion member 114, and the reinforcing member 117 are formed of a flexible material, the material is not particularly limited, and examples thereof include various thermoplastic elastomers such as styrene-based, polyolefin-based, polyurethane-based, polyester-based, polyimide-based, polyimide-based, polybutadiene-based, trans polyisoprene-based, fluorine rubber-based, and chlorinated polyethylene-based. One or a combination of two or more of these (polymer alloy, polymer blend, laminate, and the like) can also be used. A hydrophilic lubricating coating layer that exhibits lubricity when wet can be disposed on the outer surface of the sheath 110.

As illustrated in FIG. 4, the hub 160 includes a hub main body 161 having a hollow shape, a connector case 165c connected to the proximal end of the hub main body 161, a port 162 communicating with the inside of the hub main body 161, projections 163a and 163b for determining the position (direction) of the hub 160 when connecting to the external device 300, a connection pipe 164b holding the drive shaft 140, a bearing 164c rotatably supporting the connection pipe 164b, a sealing member 164a preventing the priming solution from leaking from between the connection pipe 164b and the bearing 164c toward the proximal end side, and a connector portion 165 in which an electrode terminal 165a and an optical connector 165b connected to the external device 300 are disposed.

The inner shaft 130 is connected to the distal portion of the hub main body 161. The drive shaft 140 is pulled out from or extends out from the inner shaft 130 inside the hub main body 161.

The port 162 is connected to an injection device S (refer to FIG. 1) for injecting a priming solution when performing the priming processing. The injection device S is provided with a connector S1 connected to the port 162, a tube S2 connected to the connector S1, a three-way stopcock S3 connected to the tube S2, and a first syringe S4 and a second syringe S5 which are connected to the three-way stopcock S3 and can inject the priming solution into the port 162. The second syringe S5 has a larger capacity than that of the first syringe S4, and is a syringe used as an auxiliary in a case where the amount of the priming solution injected by the first syringe S4 is insufficient.

The connection pipe 164b holds the drive shaft 140 in order to transmit the rotation of the electrode terminal 165a and the optical connector 165b which are rotationally driven by the external device 300 to the drive shaft 140. The electric signal cable 142 and the optical fiber 143 (refer to FIG. 3) are inserted into the connection pipe 164*b*.

The connector portion 165 is provided with the electrode terminal 165*a* electrically connected to the electric signal cable 142 and the optical connector 165*b* connected to the optical fiber. A reception signal in the ultrasound transmitter and receiver 145*a* is transmitted to the external device 300 via the electrode terminal 165*a*, subjected to the predetermined processing, and displayed as an image. A reception signal in the optical transmitter and receiver 145*b* is transmitted to the external device 300 via the optical connector 165*b*, subjected to the predetermined processing, and displayed as an image.

Referring again to FIG. 1, the image diagnosis catheter 100 is connected to the external device 300 and driven.

As described above, the external device 300 is connected to the connector portion 165 provided on the proximal end of the hub 160.

In addition, the external device 300 includes a motor 300*a* that is a power source for rotating the drive shaft 140, and a motor 300*b* that is a power source for moving the drive shaft 140 in the axial direction. The rotational motion of the motor 300*b* is converted into axial motion by a direct motion conversion mechanism 300*c* connected to the motor 300*b*. As the direct motion conversion mechanism 300*c*, for example, a ball screw, a rack and pinion mechanism, or the like can be used.

The operation of the external device 300 is controlled by a control apparatus 301 electrically connected to the external device. The control apparatus 301 includes a central processing unit (CPU) and a memory as main components. The control apparatus 301 is electrically connected to a monitor 302.

Figure 5:
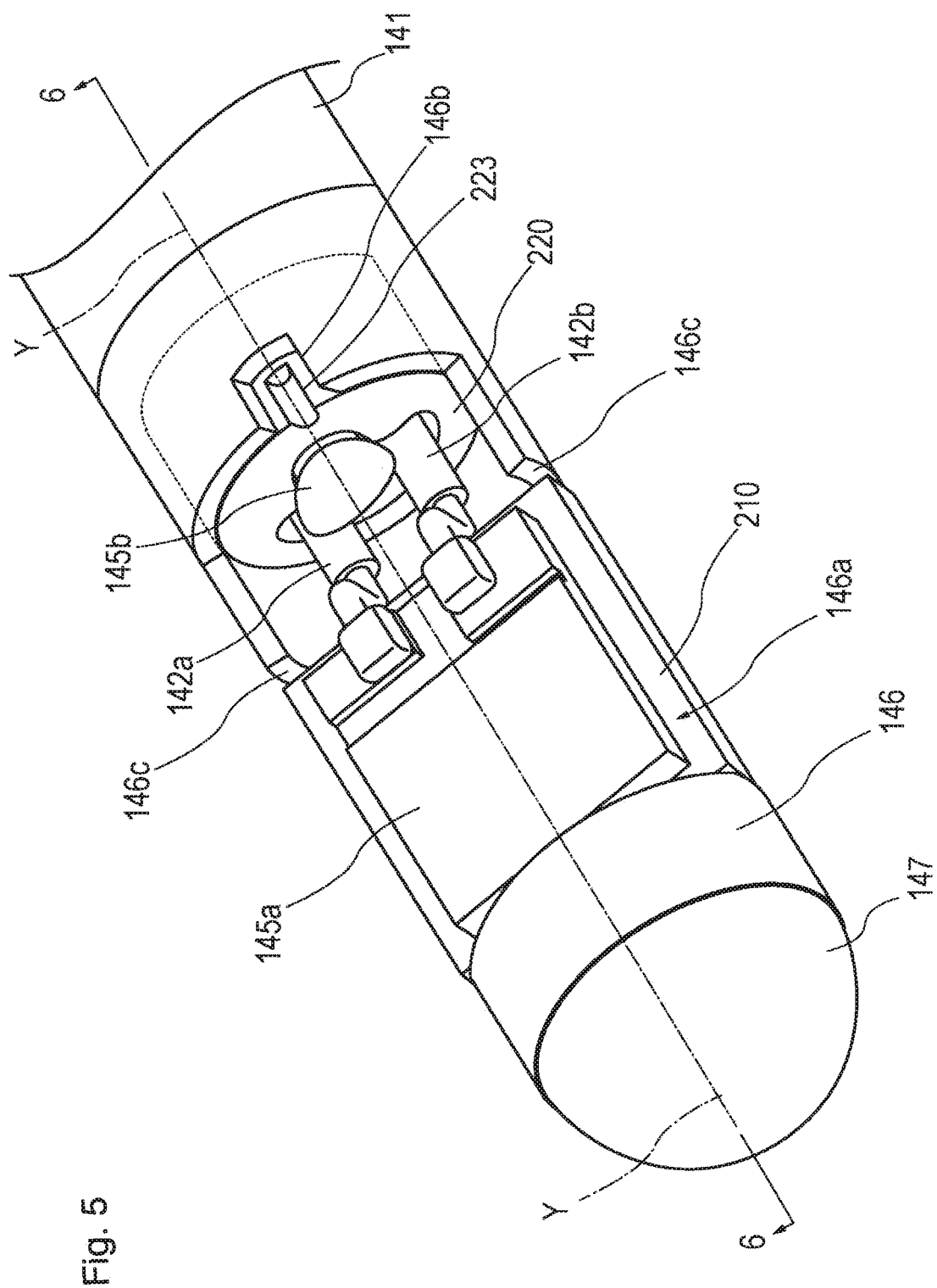
FIG. 5 is an enlarged perspective view illustrating a configuration of a housing and a positioning member of the image diagnosis catheter according to the embodiment.

Next, a positioning mechanism of the ultrasound transmitter and receiver 145*a* and the optical transmitter and receiver 145*b* in the housing 146 will be described with reference to FIGS. 5 to 8. In the following description, a side of the housing 146 where the opening portion 146*a* is provided (upper side in FIG. 6) is referred to as an "upper side". In addition, as illustrated in FIG. 5, in a case where the image diagnosis catheter 100 is not inserted into the biological lumen 900, a rotation axis in a state where the drive shaft 140 is straightened is indicated by Y. In a state where the image diagnosis catheter 100 is inserted into the biological lumen 900, the rotation axis of the drive shaft can be bent along a bent shape of the biological lumen 900.

Figure 6:
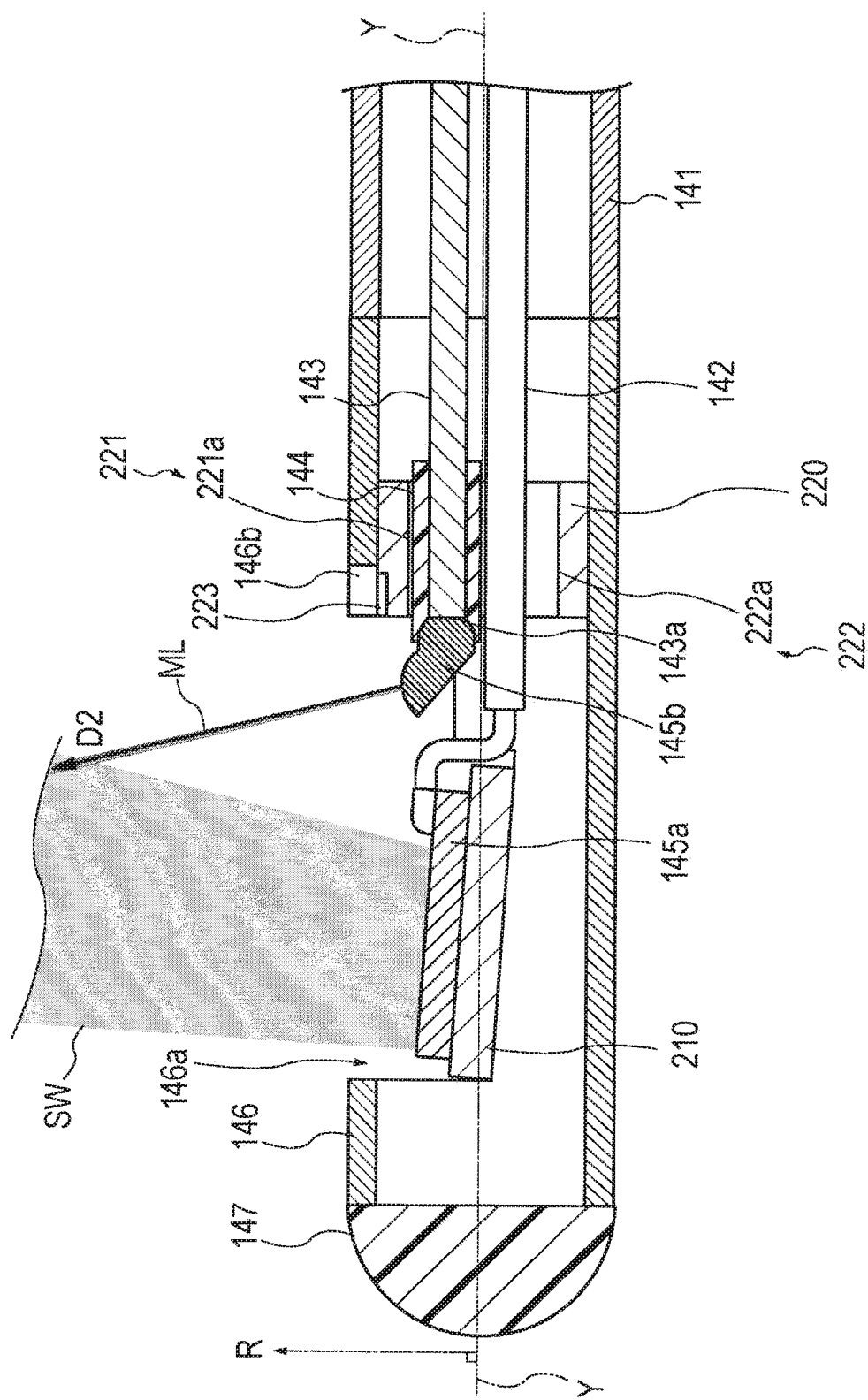
FIG. 6 is an enlarged cross-sectional view taken along line 6-6 of FIG. 5.
Figure 7:
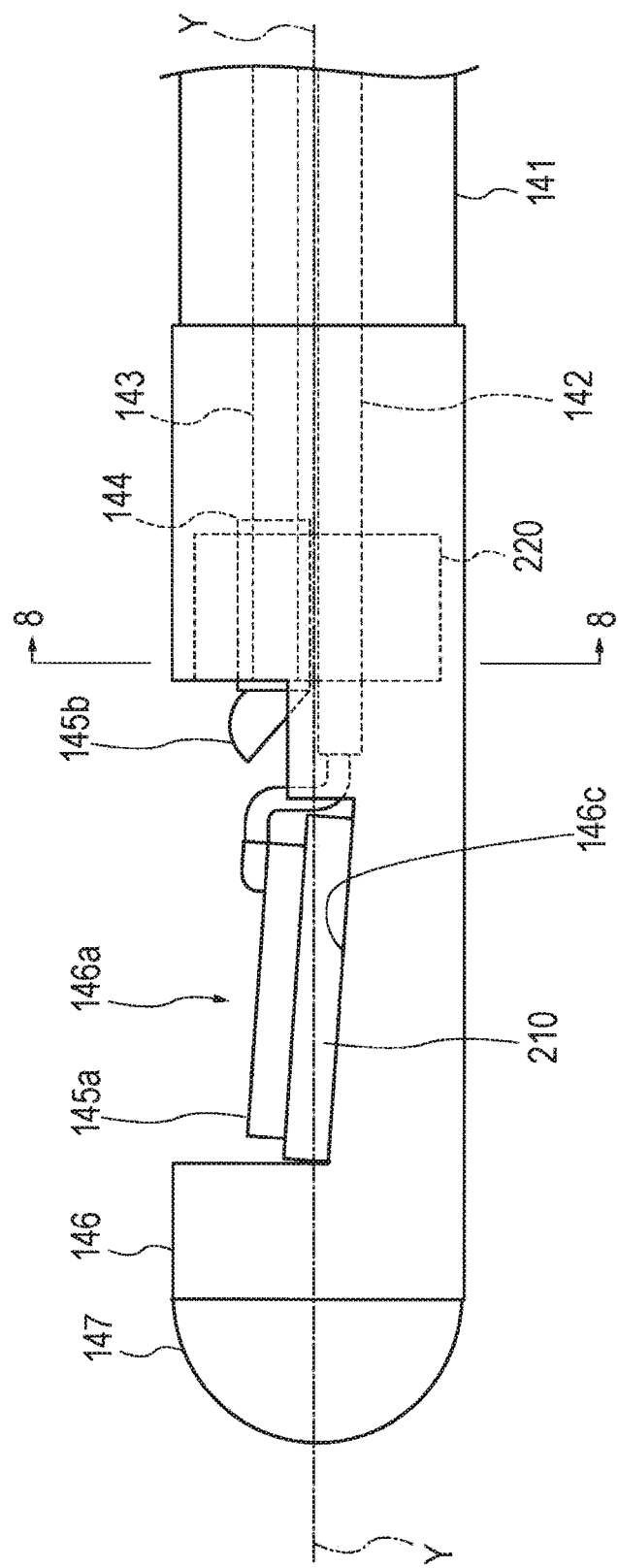
FIG. 7 is an enlarged side view illustrating the configuration of the housing and the positioning member of the image diagnosis catheter according to the embodiment.

The ultrasound transmitter and receiver 145*a* is attached to a backing member 210 as illustrated in FIG. 7. The backing member 210 scatters and attenuates the ultrasound from the ultrasound transmitter and receiver 145*a* in the direction opposite to the opening portion 146*a* of the housing 146. The backing member 210 is attached to an edge portion 146*c* that surrounds the opening portion 146*a* of the housing 146. As described above, the ultrasound transmitter and receiver 145*a* is fixed to the housing 146 via the backing member 210. A method of fixing the backing member 210 to the housing 146 is not particularly limited, and can be fixed by bonding with an adhesive, for example. As illustrated in FIG. 6, the ultrasound transmitter and receiver 145*a* is fixed to the housing 146 so that the ultrasound SW is transmitted in a direction inclined toward the proximal end side with respect to a radiation direction (radial direction R) of the drive shaft 140.

The optical transmitter and receiver 145*b* is fixed to the housing 146 via a positioning member 220 as illustrated in FIG. 6. Therefore, a relative position of the optical transmitter and receiver 145*b* with respect to the ultrasound transmitter and receiver 145*a* can be determined. As a result, a transmission direction of the measurement light ML transmitted from the optical transmitter and receiver 145*b* can be determined in a fixed direction with respect to a direction of the ultrasound SW transmitted from the ultrasound transmitter and receiver 145*a*. Therefore, for example, at the time of manufacture (assembly), the relative positional relationship between the ultrasound and light of each image diagnosis catheter can be suitably maintained within a desired tolerance.

In the present embodiment, the positioning member 220 fixes the position of the optical transmitter and receiver 145*b* so that the ultrasound SW transmitted from the ultrasound transmitter and receiver 145*a* intersects with the measurement light ML transmitted from the optical transmitter and receiver 145*b*.

The positioning member 220 is fixed to the inner surface of the housing 146 on the proximal end of the housing 146. As illustrated in FIG. 5, the positioning member 220 has a cylindrical outer shape. As illustrated in FIG. 8, the positioning member 220 is provided with an optical fiber fixing portion 221 that fixes the optical fiber 143, an electric signal cable insertion portion 222 through which the electric signal cable 142 can be inserted, and a recess 223 for adjusting a position in a circumferential direction of the positioning member 220 with respect to the housing 146.

The optical fiber fixing portion 221 is provided with a concave groove portion (concave groove or groove) 221*a* into which the optical fiber 143 can be fitted. As illustrated in FIG. 6, the groove portion 221*a* penetrates the positioning member 220 in the axial direction. The optical transmitter and receiver 145*b* is connected to the distal end of the optical fiber 143 disposed so as to be inserted through the groove portion 221*a* in the axial direction. As described above, the positioning member 220 fixes the position of the optical transmitter and receiver 145*b* by fixing the optical fiber 143.

As illustrated in FIG. 5, the positioning member 220 is provided in the housing 146 so that the optical transmitter and receiver 145*b* is positioned on the rotation axis Y of the drive shaft 140 when viewed from above the housing 146. Therefore, the ultrasound transmitter and receiver 145*a* and the optical transmitter and receiver 145*b* are positioned side by side on the rotation axis Y of the drive shaft 140 when viewed from above the housing 146. In addition, as illustrated in FIG. 6, the positioning member 220 is fixed to the housing 146 so that the curved surface of the ball lens constituting the optical transmitter and receiver 145*b* faces upward of the housing 146. The optical transmitter and receiver 145*b* connected to the distal end of the optical fiber 143 transmits the measurement light ML in a direction inclined toward the distal end side with respect to the radial direction R of the drive shaft 140. Therefore, the ultrasound SW transmitted from the ultrasound transmitter and receiver 145*a* intersects with the measurement light ML transmitted from the optical transmitter and receiver 145*b*.

As illustrated in FIG. 6, the ultrasound SW transmitted from the ultrasound transmitter and receiver 145*a* propagates outward of the housing 146 so as to spread slightly. In addition, similarly, the measurement light ML transmitted from the optical transmitter and receiver 145*b* also propagates outward from the housing 146 so as to spread slightly. In this specification, "ultrasound SW transmitted from the ultrasound transmitter and receiver 145*a* intersects with measurement light ML transmitted from the optical transmitter and receiver 145*b*" means that at least a propagation region of the ultrasound SW propagating with spread (region illustrated in light gray in the drawing) intersects with a propagation region of the measurement light ML with spread (region illustrated in dark gray in the drawing).

In the present embodiment, as illustrated in FIG. 10, a transmission direction D1 of the central portion of the ultrasound SW transmitted from the ultrasound transmitter and receiver 145a toward the outside of the housing 146 (wall of the biological lumen 900b) are configured to intersect with a transmission direction D2 (optical axis direction) of the central portion of the measurement light ML transmitted from the optical transmitter and receiver 145b toward the outside of the housing 146 (wall of the biological lumen 900b) at a point P where a distance from the outer surface of the housing 146 is a length L1. Therefore, for example, in a case where the image diagnosis catheter 100 is inserted into the biological lumen 900, when the image diagnosis catheter 100 is disposed at a position where the distance from the outer surface of the housing 146 to the wall of the biological lumen 900b is approximately the length L1, as illustrated in FIG. 11, an inspection region of the ultrasound SW (region illustrated in light gray) and an inspection region of the measurement light ML (region illustrated in dark gray) on the wall of the biological lumen 900b can overlap each other. The distance L1 can be appropriately set according to the average diameter of the biological lumen 900 into which the image diagnosis catheter 100 is inserted.

The ultrasound SW and the measurement light ML have a spread to some extent. Therefore, when the measurement light ML is applied to at least any portion of the region (region illustrated in light gray) where the ultrasound SW hits on the wall of the biological lumen 900b, the inspection region of the ultrasound SW and the inspection regions of the measurement light ML can overlap each other. Therefore, even when the diameter of the biological lumen 900 changes depending on the position in the extending direction of the biological lumen 900, the inspection region of the ultrasound SW and the inspection region of the measurement light ML can overlap each other.

In addition, in the present embodiment, as illustrated in FIG. 6, an interlock portion 143a is covered with a protective cover 144 in order to protect the interlock portion 143a of the optical fiber 143 and the optical transmitter and receiver 145b. Since the signal transmitter and receiver 145, the electric signal cable 142, the optical fiber 143, the positioning member 220, and the like are disposed in the housing 146, the housing 146 preferably has a larger inner diameter r2 (refer to FIG. 8(A)). However, in order to suitably maintain the slidability of the sheath 110 in the biological lumen 900, the housing 146 preferably has a small outer diameter, and it is necessary to secure a thickness to some extent in order to ensure strength. Therefore, there is a limit in forming the inner diameter r2 (refer to FIG. 8(A)) of the housing 146 to be large. Therefore, there is a limit in forming the outer diameter of the positioning member 220 accommodated in the housing 146 to be large. Therefore, when the optical fiber 143 is disposed so that the axial center of the optical fiber 143 covered with the protective cover 144 is positioned on the rotation axis Y of the drive shaft 140, due to the outer diameter r1 of the optical fiber 143 including the protective cover 144, it is difficult to secure a space (electric signal cable insertion portion 222) for disposing the electric signal cable 142 (two signal lines 142a and 142b) having a fixed outer diameter r3. Therefore, the groove portion 221a is provided at a position displaced in the transmission direction D2 of the measurement light ML transmitted from the optical transmitter and receiver 145b with respect to the rotation axis Y of the drive shaft 140. The distal portion of the optical fiber 143 is fixed at a position displaced in the transmission direction D2 of the measurement light ML transmitted from the optical transmitter and receiver 145b with respect to the rotation axis Y of the drive shaft 140. As a result, a space (electric signal cable insertion portion 222) where the electric signal cable 142 is disposed at a position opposite to the transmission direction D2 of the measurement light ML with respect to the optical fiber 143 can be secured.

The electric signal cable insertion portion 222 is provided with a hole portion (hole) 222a that is continuous with (communicates with) the groove portion 221a and provided at a position opposite to the transmission direction D2 of the measurement light ML. The hole portion 222a is formed by hollowing out the positioning member 220 in a substantially semicircular shape. In the hole portion 222a, two signal lines 142a and 142b are respectively disposed on both sides in a direction (left and right direction in the drawing) orthogonal to the transmission direction D2 of the measurement light ML.

Figure 8A:
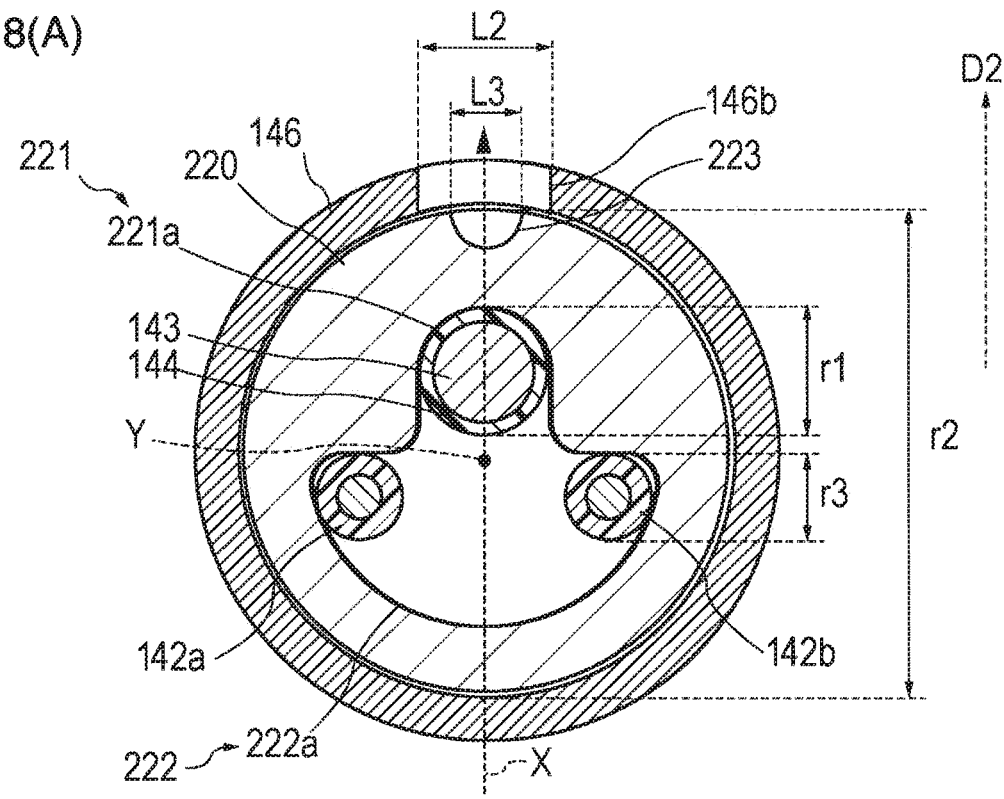
FIGS. 8(A) and 8(B) are enlarged cross-sectional views taken along the section line 8-8 in FIG. 7.
Figure 8B:
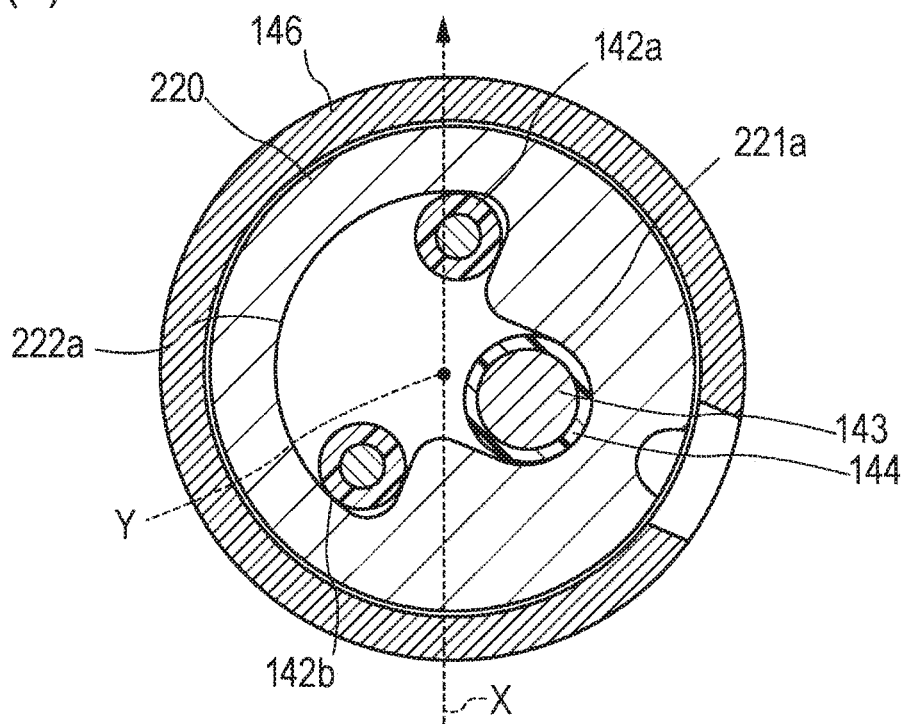

The recess 223 is provided in a certain region of the outer surface of the positioning member 220, which is located downstream in the direction D2 of transmission of the measurement light ML. In addition, as illustrated in FIG. 5, the housing 146 is provided with a notch 146b (corresponding to a "penetration portion") that penetrates a portion on the proximal end of the opening portion 146a (portion for accommodating the positioning member 220) in the thickness direction. As illustrated in FIG. 8, the recess 223 provided in the positioning member 220 and the notch 146b provided in the housing 146 are provided at positions that overlap one another in the radial direction. For example, as shown in FIGS. 8(A) and 8(B), a plane perpendicular to the rotational axis Y of the drive shaft and passing through the notch 146b also passes through the recess 223. In addition, a width L2 of the notch 146b (length along the circumferential direction of the housing 146) is longer than a width L3 of the recess 223 (maximum length along the circumferential direction of the positioning member 220). Therefore, for example, when the image diagnosis catheter 100 is assembled (manufactured), a jig such as a needle or tweezers is inserted from the notch 146b and hooked into the recess 223, the positioning member 220 is rotated with respect to the housing 146, and the position in the circumferential direction of the positioning member 220 with respect to the housing 146 is finely adjusted so that the ultrasound SW intersects the measurement light ML. Thereafter, the positioning member 220 can be fixed to the housing 146. A method of fixing the positioning member 220 to the housing 146 is not particularly limited, and for example, the positioning member 220 can be bonded by an adhesive. In this case, for example, the positioning member 220 is rotated while injecting the adhesive by way of the notch 146b and the adhesive is spread over the peripheral surface of the positioning member 220. Therefore the positioning member 220 can be fixed to the housing 146.

It is preferable that the positioning member 220 is made of a material having a rigidity that does not deform when the optical fiber 143 is pressed. By forming the positioning member 220 with such a material, for example, compared with a case where the optical fiber 143 is directly fixed to the housing 146 with an adhesive, the relative position of the optical transmitter and receiver 145b with respect to the ultrasound transmitter and receiver 145a can be easily determined, when the image diagnosis catheter 100 is assembled (manufactured).

In addition, it is preferable that the positioning member 220 includes or is made of (fabricated from) a material having a contrast property (X-ray opaque material) under X-ray fluoroscopy. When the positioning member 220 includes such a material, the operator can easily grasp the positions of the positioning member 220 and the optical transmitter and receiver 145b provided at the distal end thereof under X-ray fluoroscopy. In particular, in the present embodiment, since the positioning member 220 is provided with the groove portion 221a and the hole portion 222a, the thickness of the positioning member 220 varies depending on the position in the circumferential direction. For example, as illustrated in FIG. 8(A), in a case where X-rays are irradiated from the lower side to the upper side as indicated by the arrow X in the state where the groove portion 221a is disposed on the upper side, since the X-rays pass through both the groove portion 221a and the hole portion 222a, the thickness of the positioning member 220 in the portion through which X-rays pass is thin, and the positioning member 220 is displayed relatively thinly under X-ray fluoroscopy. At the position where the positioning member 220 is rotated with respect to FIG. 8(A) (position illustrated in FIG. 8(B)), since the X-rays pass only through the hole portion 222a, the thickness of the positioning member 220 in the portion through which X-rays pass is relatively thick, and the positioning member 220 is displayed relatively dark under X-ray fluoroscopy. As described above, when the operator rotates the drive shaft 140 under X-ray fluoroscopy, the positioning member 220 also rotates in conjunction with the rotation, and the region where the positioning member 220 is provided changes in shade in conjunction with the rotation. Therefore, the operator can more easily grasp the position of the positioning member 220 under X-ray fluoroscopy.

Note that, for example, Pt, Au, a Pt—Ir alloy, or the like can be used as a material having a rigidity that does not deform when the optical fiber 143 is pressed and having a contrast property under X-ray fluoroscopy. These noted materials can thus be used to fabricate the positioning member 220.

Next, an example of use in a case where the image diagnosis catheter 100 is inserted into a blood vessel 900 (biological lumen) will be described.

First, the user connects the injection device S for injecting the priming solution to the port 162 with the hub 160 pulled to the most proximal end (refer to FIG. 2B), and pushes a plunger of the first syringe S4 to inject the priming solution into the lumen 110a of the sheath 110. In a case where the amount of the priming solution injected by the first syringe S4 is insufficient, the priming solution is injected into the lumen 110a of the sheath 110 by pushing a plunger of the second syringe S5.

When the priming solution is injected into the lumen 110a, the priming solution is discharged to the outside of the sheath 110 through the communication passage 117a and the communication hole 116 illustrated in FIG. 3, and a gas such as air can be discharged from the inside of the sheath 110 to the outside together with the priming solution (priming processing).

After the priming processing, the user connects the external device 300 to the connector portion 165 of the image diagnosis catheter 100 as illustrated in FIG. 1. The user pushes the hub 160 until the hub 160 attaches the proximal end of the unit connector 150 (refer to FIG. 2(A)), and moves the signal transmitter and receiver 145 to the distal end side.

Next, the user creates a port on the wrist or thigh of a patient (living body) using an introducer kit. Next, a first guide wire (not illustrated) is inserted through the port to the vicinity of a coronary artery entrance of the heart of the patient. Next, a guiding catheter 800 is introduced to the coronary artery entrance through the first guide wire. Next, the first guide wire is removed, and a second guide wire W is inserted into a lesion area through the guiding catheter 800. Next, the image diagnosis catheter 100 is inserted into the lesion area along the second guide wire W.

Figure 9A:
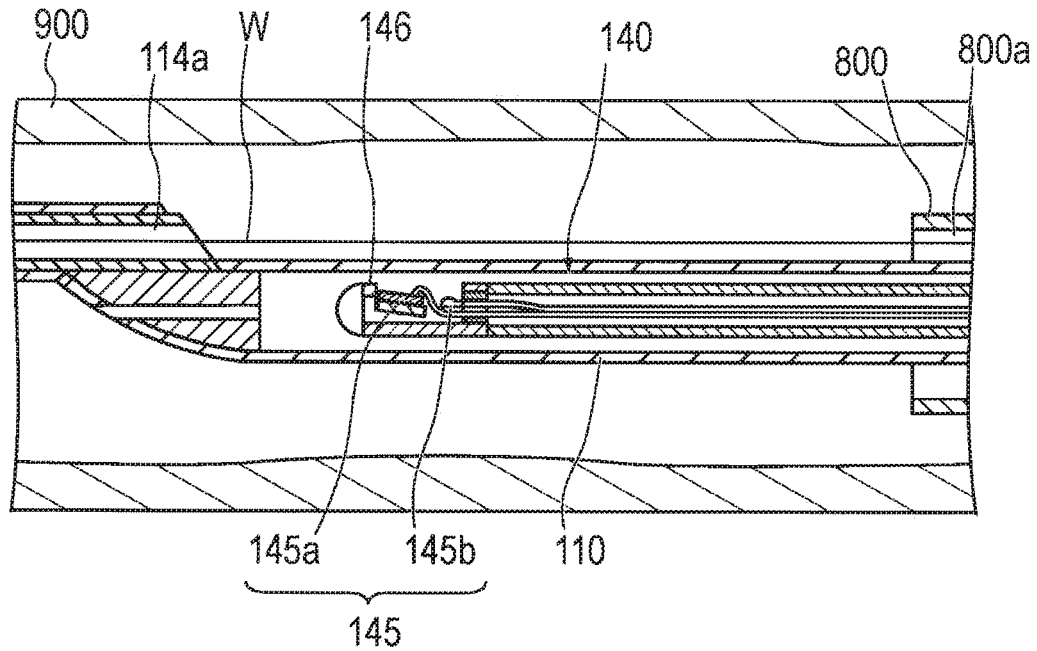
FIGS. 9(A) and 9(B) are schematic views illustrating an example of use of the image diagnosis catheter according to the embodiment.
Figure 9B:
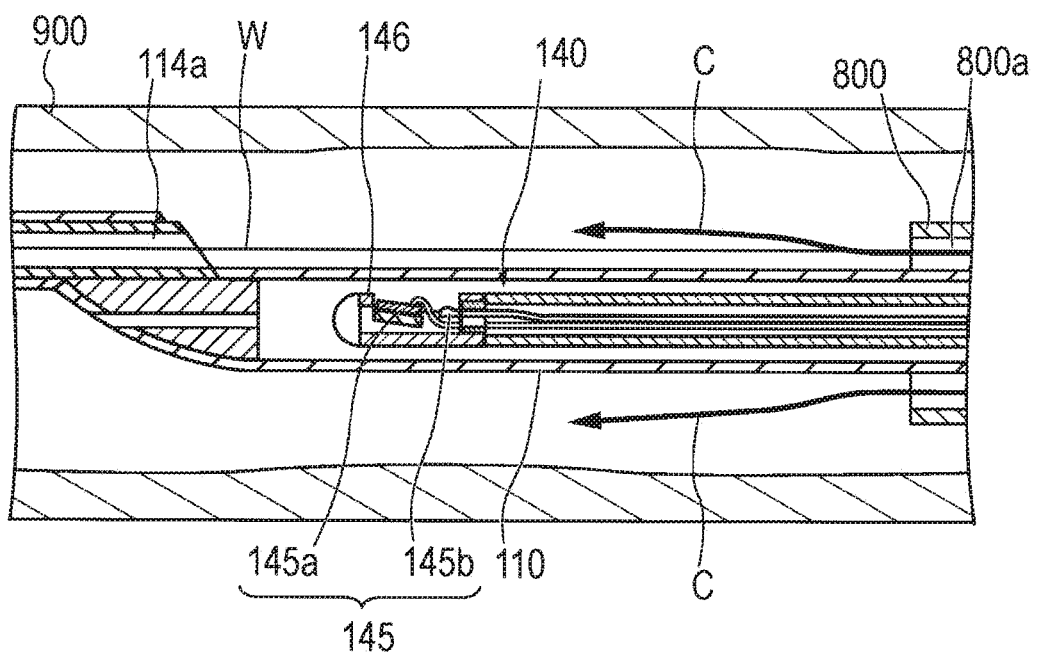

Next, as illustrated in FIG. 9(A), the image diagnosis catheter 100 is advanced along the lumen 800a and protruded from a distal opening portion of the guiding catheter 800. Thereafter, while the second guide wire W is inserted through the guide wire lumen 114a, the image diagnosis catheter 100 is further pushed along the second guide wire W to be inserted into a target position in the blood vessel 900. As the guiding catheter 800, a known guiding catheter provided with a port (not illustrated) to which a syringe (not illustrated) can be connected at a proximal portion can be used.

Next, the blood in the blood vessel 900 is temporarily replaced with a flush solution such as a contrast agent. Similarly to the priming processing described above, the syringe containing the flush solution is connected to the port of the guiding catheter 800, and the plunger of the syringe is pushed to inject the flush solution into the lumen 800a of the guiding catheter 800. As illustrated by an arrow C in FIG. 9(B), the flush solution passes through the lumen 800a of the guiding catheter 800 and is introduced into the blood vessel 900 through the distal opening portion. The blood around the distal portion of the sheath 110 is washed away by the introduced flush solution, and the flush solution is filled around the distal portion of the sheath 110. In the mode of acquiring a tomographic image only by IVUS, the above-described step of replacing blood with the flush solution can be omitted.

When obtaining a tomographic image at a target position in the blood vessel 900, the signal transmitter and receiver 145 moves to the proximal end side while rotating with the drive shaft 140 (pull-back operation). Simultaneously with the pull-back operation, as illustrated in FIG. 10, the ultrasound transmitter and receiver 145a transmits the ultrasound SW toward a blood vessel wall 900b and receives the ultrasound reflected by the blood vessel wall 900b. In addition, the optical transmitter and receiver 145b simultaneously transmits the measurement light ML toward the blood vessel wall 900b and receives the reflected light reflected by the blood vessel wall 900b As described above, since the ultrasound SW transmitted from the ultrasound transmitter and receiver 145a intersects with the measurement light ML transmitted from the optical transmitter and receiver 145b, a region to be inspected by the ultrasound in the living body and a regions to be inspected with the light can be overlapped.

The rotation and movement operation of the drive shaft 140 is controlled by the control apparatus 301. The connector portion 165 provided in the hub 160 is rotated while being connected to the external device 300, and the drive shaft 140 is rotated in conjunction with this rotation.

In addition, the signal transmitter and receiver 145 transmits the ultrasound and light into the body based on the signal sent from the control apparatus 301. A signal corresponding to the reflected wave and the reflected light received by the signal transmitter and receiver 145 is sent to the control apparatus 301 via the drive shaft 140 and the external device 300. The control apparatus 301 generates a tomographic image of the body-cavity based on the signal sent from the signal transmitter and receiver 145 and displays the generated image on the monitor 302.

Hereinbefore, the image diagnosis catheter 100 according to the present embodiment includes the rotatable drive shaft 140, the sheath 110 into which the drive shaft 140 is inserted, the housing 146 provided at the distal end of the drive shaft 140 and accommodating the ultrasound transmitter and receiver 145a and the optical transmitter and receiver 145b, and the positioning member 220 fixed to the housing 146 and fixes the relative position of the optical transmitter and receiver 145b with respect to the ultrasound transmitter and receiver 145a. That is, the ultrasound transmitter and receiver and the optical transmitter and receiver are positionally fixed (fixed in position) relative to one another by virtue of the positioning member.

As described above, the relative position of the optical transmitter and receiver 145b with respect to the ultrasound transmitter and receiver 145a is fixed. Therefore, the transmission direction of the measurement light ML with respect to the transmission direction of the ultrasound SW can be kept in a fixed direction. As a result, for example, at the time of manufacture (assembly), the relative position of the measurement light ML with respect to the ultrasound SW of each image diagnosis catheter 100 can be kept within a desired tolerance.

In addition, the positioning member 220 fixes the relative position of the optical transmitter and receiver 145b with respect to the ultrasound transmitter and receiver 145a so that the ultrasound SW transmitted from the ultrasound transmitter and receiver 145a intersects with the measurement light ML transmitted from the optical transmitter and receiver 145b. Therefore, the ultrasound can be made to intersect with light at a fixed position. In addition, the inspection region of the ultrasound SW and the inspection region of the measurement light ML in the living body can be overlapped.

In addition, the drive shaft 140 is provided with the optical fiber 143 optically connected to the optical transmitter and receiver 145b, and the positioning member 220 is provided with the optical fiber fixing portion 221 that fixes the optical fiber 143. Therefore, by fixing the optical fiber 143, the direction where the optical transmitter and receiver 145b transmits the measurement light ML can be easily adjusted.

In addition, the drive shaft 140 is provided with the electric signal cable 142 electrically connected to the ultrasound transmitter and receiver 145a, and in the positioning member 220, the electric signal cable 142 is disposed at a position opposite to the transmission direction D2 of the measurement light ML transmitted from the optical transmitter and receiver 145b with respect to the optical fiber 143. Therefore, the electric signal cable 142 can be electrically connected to the ultrasound transmitter and receiver 145a accommodated in the housing 146 without interfering with transmission and reception of light from the optical transmitter and receiver 145b.

In addition, the optical fiber fixing portion 221 fixes the optical fiber 143 at a position displaced in the transmission direction D2 of the measurement light ML transmitted from the optical transmitter and receiver 145b with respect to the rotation axis Y of the drive shaft 140. Therefore, in the limited internal space of the housing 146, the positioning member 220 can dispose the optical fiber 143 and the electric signal cable 142.

In addition, the optical fiber fixing portion 221 is provided with the concave groove portion 221a into which the optical fiber 143 can be fitted. Therefore, the position of the optical fiber 143 can be easily determined by fitting the optical fiber 143 into the groove portion 221a.

In addition, the positioning member 220 is provided with the recess 223 on the outer surface, and the housing 146 is provided with the notch 146b penetrating the housing 146 in the thickness direction at a position overlapping the recess 223 in the radial direction. Therefore, a jig such as a needle or tweezers is inserted into the notch 146b and hooked into the recess 223, so that the positioning member 220 can be fixed to the housing 146, after the position of the positioning member 220 accommodated in the housing 146 is finely adjusted.

The positioning member 220 is made of a material having a contrast property under X-ray fluoroscopy. Therefore, the operator can easily grasp the positions of the positioning member 220 and the optical transmitter and receiver 145b under X-ray fluoroscopy.

The ultrasound transmitter and receiver 145a is fixed to the housing 146. Therefore, the relative position of the optical transmitter and receiver 145b with respect to the ultrasound transmitter and receiver 145a can be easily determined.

<Modification 1>

Figure 12:
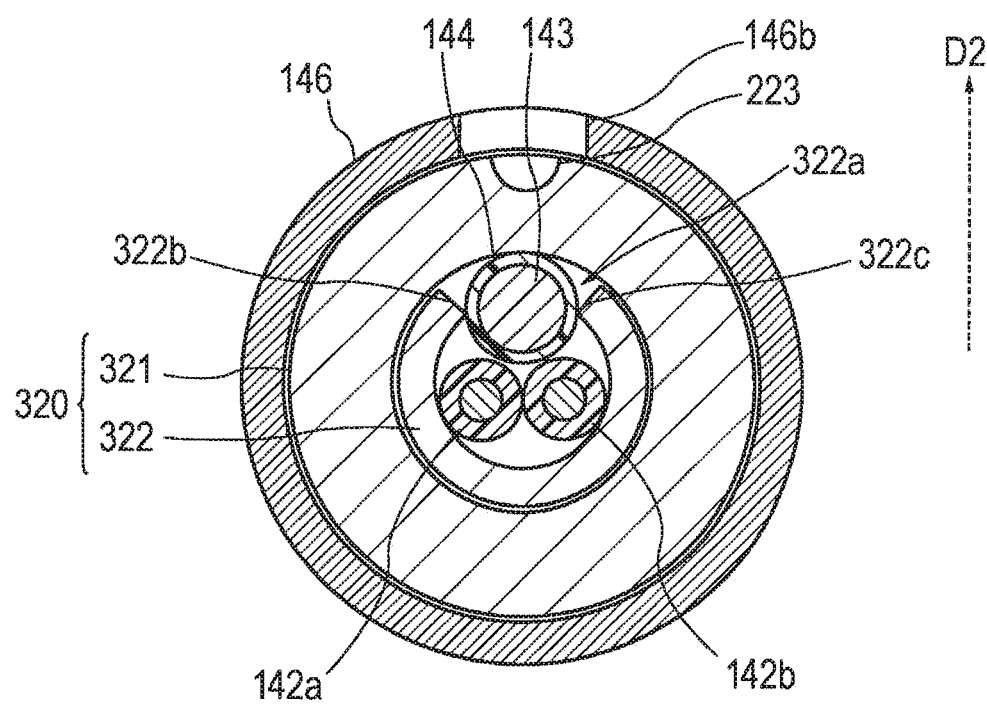
FIG. 12 is a cross-sectional view illustrating a configuration of a positioning member of an image diagnosis catheter according to Modification 1.

Next, a positioning member 320 according to Modification 1 will be described with reference to FIG. 12.

The positioning member 320 according to the Modification 1 is different from the positioning member 220 according to the above-described embodiment in that the positioning member 320 is configured by combining two members. Features in this modification that are the same as features described above are identified by the same reference numeral and a detailed description of such features is not repeated.

The positioning member 320 is provided with a cylindrical first member 321 and a second member 322 accommodated in the first member 321.

The first member 321 is accommodated in the housing 146.

The second member 322 has a shape in which an opening portion 322a is provided on the upper side of a cylindrical pipe. That is, the second member 322 has a cylindrical shape with a circumferential portion of the cylinder removed. The opening portion 322a is formed over the entire length in the axial direction of the second member 322. The optical fiber 143 is disposed so as to directly contact end portions 322b and 322c (corresponding to "first attachment portion" and "second attachment portion") on both sides across the opening portion 322a. Both end portions 322b, 322c of the second member 322 thus directly contact the optical fiber 143. In addition, the electric signal cable 142 is disposed so as to be inserted under the optical fiber 143 (side opposite to the transmission direction D2 of the measurement light ML).

As described above, the optical fiber fixing portion of the positioning member 320 according to Modification 1 is provided with the first attachment portion 322b that attaches a peripheral surface of the optical fiber 143, and the second attachment portion 322c that is spaced apart from the first attachment portion 322b and capable of interposing the optical fiber 143 with the first attachment portion 322b. Therefore, the position of the optical fiber 143 can be easily determined by disposing the optical fiber 143 between the first attachment portion 322b and the second attachment portion 322c.

<Modification 2>

Figure 13:
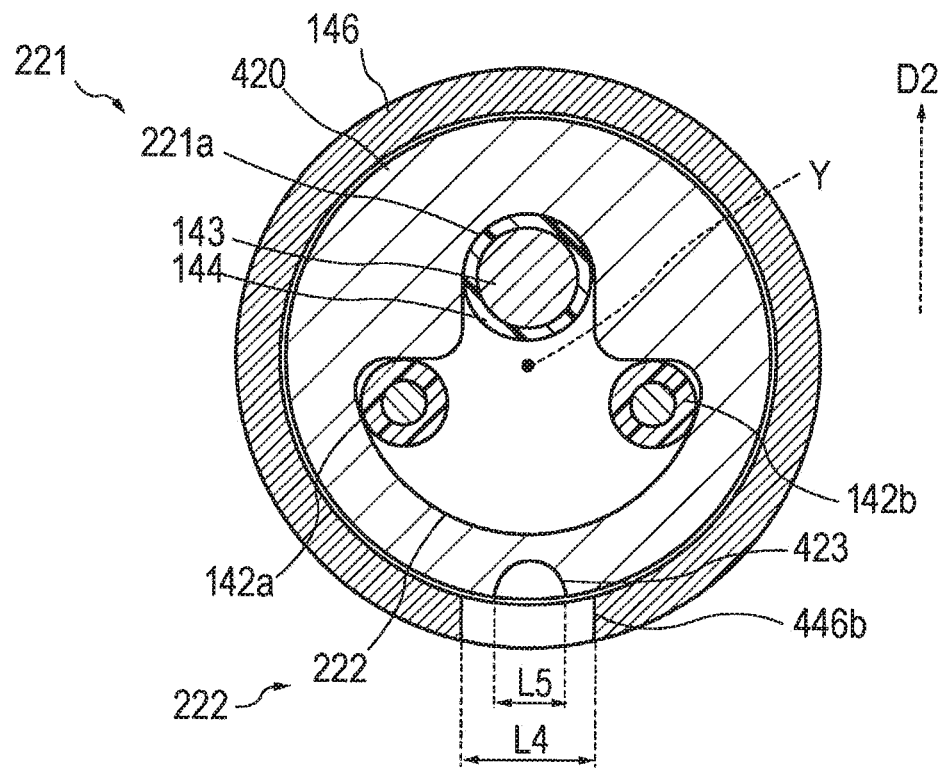
FIG. 13 is a cross-sectional view illustrating a configuration of a positioning member of an image diagnosis catheter according to Modification 2.

Next, a positioning member 420 according to Modification 2 will be described with reference to FIG. 13.

The positioning member 420 according to Modification 2 is different from the positioning member 220 according to the above-described embodiment in the position where a recess 423 is provided. In the description below, features that are the same or similar to those described above are identified by the same reference numerals and a detailed description of such features is not repeated.

The recess 423 is provided in a region on the side opposite to the transmission direction D2 side of the measurement light ML of the outer surface of the positioning member 420. In addition, a through-hole 446b (corresponding to a "penetration portion") is provided on the lower side of the housing 146 so as to penetrate a portion accommodating the positioning member 220 in the thickness direction. The recess 423 provided in the positioning member 420 and the through-hole 446b provided in the housing 146 are provided at a position overlapping in the radial direction. In addition, a width L4 of the through-hole 446b (length along the circumferential direction of the housing 146) is longer than a width L5 of the recess 423 (maximum length along the circumferential direction of the positioning member 220). Therefore, for example, when the image diagnosis catheter 100 is assembled (manufactured), a jig such as a needle or tweezers is inserted from the through-hole 446b and hooked into the recess 423, and the position of the positioning member 420 with respect to the housing 146 is finely adjusted so that the ultrasound SW intersects with the measurement light ML. Thereafter, the positioning member 420 can be fixed to the housing 146.

As described above, the positions in the circumferential direction of the recess provided in the positioning member and the penetration portion provided in the housing are not particularly limited.

<Modification 3>

Figure 14:
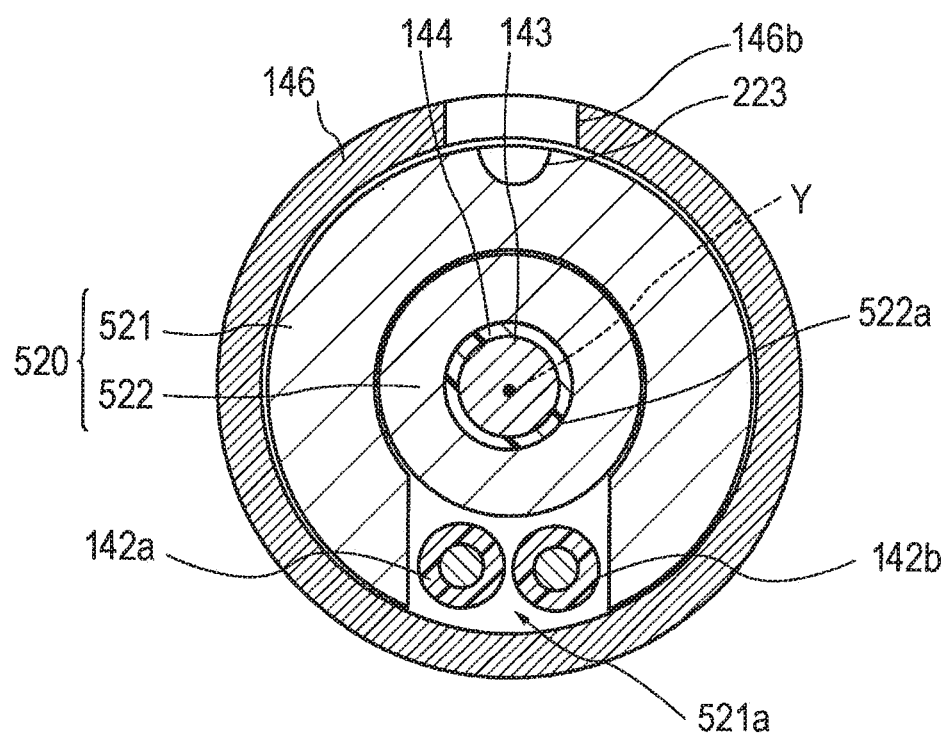
FIG. 14 is a cross-sectional view illustrating a configuration of a positioning member of an image diagnosis catheter according to Modification 3.

Next, a positioning member 520 according to Modification 3 will be described with reference to FIG. 14.

The positioning member 520 according to Modification 3 is different from the positioning member 220 according to the above-described embodiment in that the distal portion of the optical fiber 143 is fixed at a position where the central axis of the optical fiber 143 coincides with the rotation axis Y of the drive shaft 140. In the description below, features that are the same or similar to those described above are identified by the same reference numerals and a detailed description of such features is not repeated.

The positioning member 520 is provided with a first member 521 accommodated in the housing 146 and a second member 522 accommodated in the first member 521.

The first member 521 has a cylindrical pipe shape with an opening portion (opening) 521a provided on the lower side of the cylindrical pipe. An electric signal cable 142 is disposed in the opening portion 521a.

The second member 522 has a cylindrical outer shape. The second member 522 is provided with a through-hole 522a penetrating or passing through the center of the shaft (second member 522). The optical fiber 143 is fixed by being positioned in the through-hole 522a of the second member 522. Therefore, compared with the case where the optical fiber fixing portion described above is configured to include the groove portion 221a, since the peripheral surface of the optical fiber 143 is covered by the second member 522, the position of the optical fiber 143 can be further preferably be determined. In addition to the inner diameter r2 of the housing 146 being required to be relatively small as described in the above embodiment, it is necessary to secure the thickness of the second member 522 to some extent in order to maintain the strength of the second member 522 in Modification 3. Therefore, the electric signal cable 142 is disposed in the opening portion 521a of the first member 521.

Hereinbefore, the image diagnosis catheter according to the present invention has been described through the embodiment and the modifications which represent examples of the inventive image diagnosis catheter disclosed here. The present invention is not limited to the configuration described in the embodiment and the modifications, and can be appropriately changed based on the description of the scope of aspects.

For example, the description above describes an embodiment in which the image diagnosis catheter is applied to an image diagnosis catheter having the functions of the intra vascular ultra sound (IVUS) diagnosis method and the optical coherence tomography (OCT) diagnosis method. The image diagnosis catheter according to the present invention is not particularly limited as long as the image diagnosis catheter uses the ultrasound and light as inspection wave. For example, the present invention may be applied to an image diagnosis catheter having functions of an intra vascular ultra sound (IVUS) diagnosis method and an optical frequency domain imaging (OFDI) method.

In addition, for example, in the above embodiment, the aspect was described which the positioning member fixes the position of the optical transmitter and receiver with respect to the ultrasound transmitter and receiver so that the ultrasound transmitted from the ultrasound transmitter and receiver intersects with light transmitted from the optical transmitter and receiver. The configuration of the positioning member is not particularly limited as long as the relative position of the optical transmitter and receiver with respect to the ultrasound transmitter and receiver can be fixed. For example, the positioning member may be configured to fix the relative position of the optical transmitter and receiver with respect to the ultrasound transmitter and receiver so that the transmission direction of the ultrasound transmitted from the ultrasound transmitter and receiver are parallel to the transmission direction of light transmitted from the optical transmitter and receiver. In a case where the ultrasound is parallel to light, the ultrasound and light are separated by a fixed distance along the axial direction of the drive shaft. Therefore, for example, when a plurality of tomographic images are acquired by using the ultrasound and light as the inspection wave with the pull-back operation, considering that the ultrasound and light are separated by a fixed distance, from a plurality of tomographic images, it is possible to extract a tomographic image obtained by using the ultrasound acquired at the same position in the biological lumen as the inspection wave and a tomographic image acquired by using light as the inspection wave.

In addition, for example, in the above-described embodiment, the optical transmitter and receiver is described as being configured to include a ball lens. The optical transmitter and receiver is not particularly limited, as long as light in the axial direction propagating from the optical fiber is transmitted toward the biological tissue in the biological lumen, and the reflected light reflected by the biological tissue is received and propagated to the optical fiber. For example, the optical transmitter and receiver may be configured to include an optical mirror.

For example, in the above embodiment, the electric signal cable (signal line) has been described as being configured to include two cables. The electric signal cable may be configured to include, for example, a coaxial cable (one cable).

In addition, the electric signal cable may be a twisted pair cable in which two cables are wound around the optical fiber.

The detailed description above describes versions of an image diagnosis catheter representing examples of the inventive image diagnosis catheter disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST 100 image diagnosis catheter
110 sheath
140 drive shaft
142 electric signal cable (corresponding to "signal line")
143 optical fiber
145*a* ultrasound transmitter and receiver
145*b* optical transmitter and receiver
146 housing
146*b* notch (corresponding to "penetration portion")
220, 320 420, 520 positioning member
221 optical fiber fixing portion
221*a* groove portion
223, 423 recess
322*b, c* end portion (corresponding to "first attachment portion", "second attachment portion")
446*b* through-hole (corresponding to "penetration portion")
D2 direction of transmission of light
ML measurement light (corresponding to "light")
SW ultrasound
Y rotation axis of drive shaft

What is claimed is:

1. An image diagnosis catheter positionable in a living body to acquire a diagnostic image for diagnosing a site in the living body, the image diagnostic catheter comprising:
    a rotatable elongated tubular body that rotates about a rotational axis, the tubular body possessing a distal end;
    an electrical signal cable positioned inside the tubular body;
    an optical fiber positioned inside the tubular body;
    an elongated sheath in which is positioned the elongated tubular body;
    a housing mounted at the distal end of the tubular body and possessing an inner surface, the housing including an opening at a distal end portion of the housing, the housing possessing a proximal-most end and a distal-most end;
    an ultrasound transmitter and receiver connected to the electrical signal cable and configured to transmit ultrasound radially outwardly through the opening in the housing and receive reflected ultrasound through the opening in the housing for obtaining intravascular ultrasound images;
    an optical transmitter and receiver connected to the optical fiber and configured to transmit light radially outwardly through the opening in the housing and receive reflected light through the opening in the housing for obtaining tomographic images; and
    a positioning member having an outer surface facing the inner surface of the housing, the positioning member having a proximal-most end portion and a distal-most end portion, the positioning member being fixed inside the housing at a location such that at least a part of the distal-most end portion of the positioning member is proximal of the proximal-most end of the opening in the housing, the positioning member housing both the electrical signal cable and the optical fiber in a manner that positionally fixes the ultrasound transmitter and receiver and the optical transmitter and receiver relative to one another so that a region of the living body inspected by the ultrasound overlaps a region in the living body inspected by the light.

2. The image diagnosis catheter according to claim 1, wherein positioning member positionally fixes the optical transmitter and receiver relative to the ultrasound transmitter and receiver so that the ultrasound transmitted from the ultrasound transmitter and receiver intersects the light transmitted from the optical transmitter and receiver.

3. The image diagnosis catheter according to claim 1, wherein positioning member positionally fixes the optical transmitter and receiver relative to the ultrasound transmitter and receiver so that the ultrasound transmitted from the ultrasound transmitter and receiver and the light transmitted from the optical transmitter and receiver are parallel to each other.

4. The image diagnosis catheter according to claim 1, wherein the positioning member locates the electrical signal cable at a position spaced from the optical fiber in a direction opposite to a transmission direction of the light transmitted from the optical transmitter and receiver.

5. The image diagnosis catheter according to claim 1, wherein the positioning member includes an optical fiber fixing portion that fixes the optical fiber to thereby fix the position of the optical transmitter and receiver, wherein the optical fiber fixing portion fixes the optical fiber at a position displaced in a transmission direction of light transmitted from the optical transmitter and receiver with respect to the rotation axis of the tubular member.

6. The image diagnosis catheter according to claim 1, wherein the positioning member includes an optical fiber fixing portion that fixes the optical fiber to thereby fix the position of the optical transmitter and receiver, wherein the optical fiber fixing portion includes a concave groove portion in which the optical fiber is fitted.

7. The image diagnosis catheter according to claim 1, wherein the positioning member includes a cylindrical member with a circumferential portion of the cylinder removed so that the cylindrical member includes two spaced apart attachment portions between which is positioned the optical fiber, the two spaced apart attachment portions both directly contacting the optical fiber.

8. The image diagnosis catheter according to claim 1, wherein the positioning member possesses an outer surface provided with a recess, and the housing includes a penetration portion which penetrates through the housing, is proximal of the opening in the housing and is aligned with recess in the outer surface of the positioning member.

9. An image diagnosis catheter positionable in a living body to acquire a diagnostic image for diagnosing a site in the living body, the image diagnostic catheter comprising:
    an elongated tubular body that rotates about a rotational axis, the tubular body possessing a distal end;
    an electrical signal cable positioned inside the tubular body;
    an optical fiber positioned inside the tubular body;
    an elongated sheath in which is positioned the elongated tubular body;

a housing mounted at the distal end of the tubular body, the housing possessing an inner surface and including an opening at a distal end portion of the housing;

an ultrasound transmitter and receiver connected to the electrical signal cable and configured to transmit and receive ultrasound through the opening in the housing;

an optical transmitter and receiver connected to the optical fiber and configured to transmit and receive light through the opening in the housing;

a positioning member that possesses an outer surface and that is fixed to the inner surface of the housing so that the positioning member is proximal of the opening in the housing, the positioning member including an interior accommodating the electrical signal cable and the optical fiber so that the ultrasound transmitter and receiver and the optical transmitter and receiver are positionally fixed relative to one another;

the housing including a notch passing through the housing;

the outer surface of the positioning member including a recess; and a plane that is perpendicular to the rotational axis of the tubular body passes through both the notch in the housing and the recess in the outer surface of the positioning member.

10. An image diagnosis catheter positionable in a living body, the image diagnosis catheter comprising:

a sheath;

a rotatable drive shaft positioned inside the sheath, the drive shaft possessing a distal end;

a housing positioned at the distal end of the drive shaft and accommodating both an ultrasound transmitter and receiver that transmits ultrasound radially outwardly and receives reflected ultrasound for obtaining intravascular ultrasound images and an optical transmitter and receiver that transmits light radially outwardly and receives reflected light for obtaining tomographic images, the housing possessing an inner surface; and a positioning member having an outer surface facing the inner surface of the housing, the positioning member being fixed to the housing, the positioning member including a portion extending between opposite ends of the positioning member and through which passes an electrical signal cable connected to the ultrasound transmitter and receiver and an optical fiber connected to the optical transmitter and receiver, the portion of the positioning member being configured to positionally fix the optical fiber and the optical transmitter and receiver relative to the electrical signal cable and the ultrasound transmitter and receiver so that a region of the living body inspected by the ultrasound overlaps a region in the living body inspected by the light, the positioning member being made of a material having X-ray contrast properties.

11. The image diagnosis catheter according to claim 10, wherein the portion of the positioning member fixes the relative position of the optical transmitter and receiver with respect to the ultrasound transmitter and receiver so that the ultrasound transmitted from the ultrasound transmitter and receiver intersects the light transmitted from the optical transmitter and receiver.

12. The image diagnosis catheter according to claim 10, wherein the portion of the positioning member fixes the relative position of the optical transmitter and receiver with respect to the ultrasound transmitter and receiver so that the ultrasound transmitted from the ultrasound transmitter and receiver and the light transmitted from the optical transmitter and receiver are parallel to each other.

13. The image diagnosis catheter according to claim 10, wherein the drive shaft includes an optical fiber connected to the optical transmitter and receiver, and the portion of the positioning member includes an optical fiber fixing portion that fixes the optical fiber.

14. The image diagnosis catheter according to claim 13, wherein the drive shaft includes a signal line electrically connected to the ultrasound transmitter and receiver, and the portion of the positioning member locates the electrical signal cable at a position spaced from the optical fiber in a direction opposite to a transmission direction of the light transmitted from the optical transmitter and receiver.

15. The image diagnosis catheter according to claim 13, wherein the optical fiber fixing portion fixes the optical fiber at a position displaced in a transmission direction of light transmitted from the optical transmitter and receiver with respect to the rotation axis of the tubular member.

16. The image diagnosis catheter according to claim 13, wherein the optical fiber fixing portion includes a concave groove portion into which the optical fiber is fitted.

17. The image diagnosis catheter according to claim 13, wherein the optical fiber fixing portion includes a first attachment portion that directly contacts a peripheral surface of the optical fiber, and a second attachment portion that is spaced apart from the first attachment portion and is positioned so that the optical fiber is positioned between the first attachment portion and the second attachment portion.

18. The image diagnosis catheter according to claim 10, wherein the positioning member is accommodated in the housing, the outer surface of the positioning member being provided with a recess, and the housing includes a penetration portion which penetrates through a portion of the housing accommodating the positioning member in a thickness direction.

19. The image diagnosis catheter according to claim 13, wherein the ultrasound transmitter and receiver is fixed to the housing.

20. The image diagnosis catheter according to claim 10, wherein the housing includes a distal end portion at which is located an opening through which pass the light and the ultrasound, the positioning member possessing a distal-most end portion located proximal of a proximal-most end of the opening in the housing.

* * * * *